(12) United States Patent
Tanaka et al.

(10) Patent No.: US 7,838,033 B2
(45) Date of Patent: Nov. 23, 2010

(54) COMPOSITION FOR RAPID DISINTEGRATING TABLET IN ORAL CAVITY

(75) Inventors: Nobukazu Tanaka, Nakaniikawa-gun (JP); Yoshiro Nagai, Nakaniikawa-gun (JP); Hiroshi Kawaguchi, Nakaniikawa-gun (JP); Tadashi Fukami, Nakaniikawa-gun (JP); Terumasa Hosokawa, Nakaniikawa-gun (JP)

(73) Assignee: Fuji Chemical Industry Co., Ltd., Nakaniikawa-gun (JP)

( * ) Notice: Subject to any disclaimer, the term of this patent is extended or adjusted under 35 U.S.C. 154(b) by 1614 days.

(21) Appl. No.: 10/945,049

(22) Filed: Sep. 21, 2004

(65) Prior Publication Data

US 2005/0106240 A1 May 19, 2005

(30) Foreign Application Priority Data

Oct. 15, 2003 (JP) ............... 2003-355076
Aug. 16, 2004 (JP) ............... 2004-236573

(51) Int. Cl.
*A61K 9/20* (2006.01)
*A61K 9/22* (2006.01)
*A61K 9/26* (2006.01)

(52) U.S. Cl. ............... 424/469; 424/464; 424/465; 424/468

(58) Field of Classification Search ............... 424/440, 424/466
See application file for complete search history.

(56) References Cited

U.S. PATENT DOCUMENTS

| 5,527,540 A * | 6/1996 | Gergely et al. ............... 424/466 |
| 5,637,313 A * | 6/1997 | Chau et al. ............... 424/440 |
| 2001/0023252 A1 * | 9/2001 | Al-Ghazawi et al. ........ 514/321 |
| 2002/0076437 A1 | 6/2002 | Kothari et al. |
| 2003/0124184 A1 | 7/2003 | Mezaache et al. |

FOREIGN PATENT DOCUMENTS

| EP | 0 826 376 A1 | 3/1998 |
| JP | 5-271054 | 10/1993 |
| JP | 7-145052 | 6/1995 |
| JP | 10-120554 | 5/1998 |
| JP | 2000-086537 | * 9/1998 |
| JP | 11-302157 | 11/1999 |
| JP | 2000-86537 | 3/2000 |
| JP | 2001-89395 | 4/2001 |
| JP | 2001-302499 | 10/2001 |
| JP | 2002-154948 | 5/2002 |
| JP | 2002-529392 | 9/2002 |
| JP | 2003-176242 | 6/2003 |
| WO | WO 95/20380 | 8/1995 |
| WO | WO 99/55373 | 11/1999 |
| WO | WO 00/57857 | 10/2000 |
| WO | WO 00/78292 A1 | 12/2000 |
| WO | WO 01/87264 A2 | 11/2001 |
| WO | WO 02/069934 A1 | 9/2002 |
| WO | WO 03/007917 A1 | 1/2003 |
| WO | WO 03/051338 | * 6/2003 |
| WO | WO 03/051338 A1 | 6/2003 |
| WO | WO 03/074085 A1 | 9/2003 |

OTHER PUBLICATIONS

Machine Translation for Japanese Patent JP 2000-086537.*
ISP Product Guide for Crospovidone/Polyplasidone.*
Sigma-Aldrich Product Data for silica gel (Davisil grade 710).*
U.S. Appl. No. 10/576,257, filed Apr. 17, 2006, Tanaka, et al.
Database WPI Section Ch, Week 200260 Derwent Publications Ltd., London, GB; AN 2002-560764 XP002415206 & JP 2002 128661 A (Chugai Pharm) May 9, 2002 *abstract*.

* cited by examiner

*Primary Examiner*—Robert A Wax
*Assistant Examiner*—Jeffrey T Palenik
(74) *Attorney, Agent, or Firm*—Oblon, Spivak, McClelland, Maier & Neustadt, L.L.P.

(57) ABSTRACT

The present invention provides rapid disintegrating tablets in oral cavity having a shortened disintegration time in oral cavity as well as a sufficient hardness with compared to rapid disintegrating tablets of the prior art.

The above objective is solved by a composition for rapid disintegrating tablets in oral cavity, wherein components (a) to (c) are contained in such manner that
(a) saccharides consisting of a combination of mannitol and xylitol is 40 to 90 parts by weight;
(b) the inorganic excipient is 1 to 30 parts by weight; and
(c) the disintegrating agent is 5 to 40 parts by weight, provided that the total amount of (a), (b) and (c) is 100 parts by weight.

29 Claims, 5 Drawing Sheets

COMPOSITION FOR RAPID DISINTEGRATING TABLET IN ORAL CAVITY

CROSS-REFERENCE TO RELATED APPLICATION

This application is related to Japanese application No. 2003-355076 filed on Oct. 15, 2003 and Japanese application No. 2004-236573 filed on Aug. 16, 2004, whose priority are claimed under 35 USC §119, the disclosure of which are incorporated by reference in its entirety.

BACKGROUND OF THE INVENTION

1. Field of the Invention

The present invention relates to a composition for rapid disintegrating tablets in oral cavity and also to rapid disintegrating tablets in oral cavity prepared from the composition.

2. Related Arts

With regard to solid preparations for oral administration, rapid disintegrating tablets in oral cavity which are rapidly disintegrated or dissolved when placed in oral cavity have been known.

With regard to such rapid disintegrating tablets in oral cavity, those containing an excipient and erythritol (Japanese Unexamined Patent Publication No. 2003-176242), those prepared by spray-drying a suspension containing an aqueous medium, calcium hydrogen phosphate and saccharides (WO 99/55373), those prepared by spray-drying a suspension containing an inorganic excipient and saccharides (Japanese Unexamined Patent Publication No. 2000-86537), those prepared by spray-drying a dispersion containing an inorganic antacid, a sugar alcohol and a disintegrating agent in an aqueous medium (Japanese Unexamined Patent Publication No. Hei 10(1998)-120554) are known.

Besides the above, there have been disclosed a method for the production of oral dissolving tablets wherein saccharides such as xylitol, a pharmacologically active ingredient and water are mixed and made into tablets (Japanese Unexamined Patent Publication No. Hei 5(1993)-271054), an orally dissolving compression-molded product comprising granulates prepared by a fluidized-bed granulation of saccharides having a low molding property together with saccharides having a high molding property as binders (WO 95/20380), a rapid disintegrating solid preparation containing an active ingredient, a saccharide having an average particle diameter of 5 μm to 90 μm, a saccharide having an average particle diameter of 90 μm to 500 μm, a disintegrating agent and cellulose (WO 00/78292), a rapid disintegrating solid preparation prepared by spray-drying one sugar alcohol and a disintegrating agent, followed by dry tabletting (WO 02/69934), etc.

SUMMARY OF THE INVENTION

An object of the present invention is to provide a composition suitable for preparing rapid disintegrating tablets in oral cavity which, as compared with those rapid disintegrating tablets in the prior arts, has a greatly shortened disintegration time in oral cavity and a sufficient hardness, and a method for producing the same, as well as to provide rapid disintegrating tablets in oral cavity prepared by using the above composition and a method for producing the same having a high productivity by means of compression molding.

The present inventors have carried out intensive studies in order to achieve the above objects and, as a result, they have unexpectedly found that tablets which are prepared by using a specific saccharide, a disintegrating agent and an inorganic excipient in a specific ratio show a significantly shortened disintegration time in oral cavity and sufficient hardness for practical use, as compared with the conventional rapid disintegrating tablets.

Therefore, the present invention provides:

(1) a composition for rapid disintegrating tablets in oral cavity comprising mannitol, xylitol, an inorganic excipient and a disintegrating agent, wherein mannitol and xylitol form complex particles and an inorganic excipient and a disintegrating agent are dispersed in the complex particles;

(2) the composition according to the above (1), wherein components (a) to (c) are contained in such manner that
(a) saccharides consisting of a combination of mannitol and xylitol are 40 to 90 parts by weight;
(b) the inorganic excipient is 1 to 30 parts by weight; and
(c) the disintegrating agent is 5 to 40 parts by weight, provided that the total amount of (a), (b) and (c) is 100 parts by weight;

(3) the composition according to the above (1) or (2), which contains 50 to 80 parts by weight of the saccharides;

(4) the composition according to the above (1) or (2), which contains 62 to 78 parts by weight of the saccharides;

(5) the composition according to any one of the above (1) to (4), wherein the ratio by weight of mannitol to xylitol is (98 to 67):(2 to 33);

(6) the composition according to any one of the above (1) to (4), wherein the ratio by weight of mannitol to xylitol is (97 to 87):(3 to 13);

(7) the composition according to any one of the above (1) to (4), wherein the ratio by weight of mannitol to xylitol is (96 to 89):(4 to 11);

(8) the composition according to any one of the above (1) to (7), which contains 2 to 15 parts by weight of the inorganic excipient;

(9) the composition according to any one of the above (1) to (7), which contains 2 to 9 parts by weight of the inorganic excipient;

(10) the composition according to any one of the above (1) to (7), which contains 3 to 8 parts by weight of the inorganic excipient;

(11) the composition according to any one of the above (1) to (10), wherein the inorganic excipient is a pharmaceutically acceptable inorganic compound containing any of aluminum, magnesium and calcium;

(12) the composition according to the above (11), wherein the inorganic excipient is selected from magnesium aluminometasilicate, magnesium aluminosilicate, calcium hydrogen phosphate, talc, dry aluminum hydroxide gel, hydrotalcite, calcium carbonate and calcium silicate;

(13) the composition according to the above (11), wherein the inorganic excipient is selected from magnesium aluminometasilicate, calcium carbonate, hydrotalcite and calcium hydrogen phosphate;

(14) the composition according to any one of the above (1) to (13), which contains 10 to 36 parts by weight of the disintegrating agent;

(15) the composition according to any one of the above (1) to (13), which contains 16 to 35 parts by weight of the disintegrating agent;

(16) the composition according to any one of the above (1) to (13), which contains 18 to 34 parts by weight of the disintegrating agent;

(17) the composition according to any one of the above (1) to (16), wherein the disintegrating agent is selected from crospovidone, low-substituted hydroxypropyl cellulose, croscarmellose sodium and crystalline cellulose;

(18) the composition according to any one of the above (1) to (16), wherein the disintegrating agent is selected from crospovidone and crystalline cellulose;

(19) the composition according to any one of the above (1) to (18), which contains 5 to 15 parts by weight of crospovidone and 10 to 22 parts by weight of crystalline cellulose as the disintegrating agent;

(20) the composition according to any one of the above (1) to (18), which contains 6 to 13 parts by weight of crospovidone and 12 to 21 parts by weight of crystalline cellulose as the disintegrating agent;

(21) the composition according to any one of the above (1) to (20), wherein the complex particles form a solid dispersion and a fine disintegrating agent and a fine inorganic excipient are dispersed in the solid dispersion;

(22) the composition according to the above (21), wherein the disintegrating agent and the inorganic excipient have an average particle diameter of 1 to 40 μm, respectively;

(23) the composition according to any one of the above (1) to (22), wherein an endothermic peak of the saccharides measured by a differential scanning colorimeter is shifted to a low temperature side by 0.5 to 19° C. compared to an endothermic peak measured from mannitol only;

(24) the composition according to any one of the above (1) to (22), wherein an endothermic peak of the saccharides measured by a differential scanning colorimeter is shifted to a low temperature side by 1 to 9° C. compared to an endothermic peak measured from mannitol only;

(25) the composition according to any one of the above (1) to (22), wherein an endothermic peak of the saccharides measured by a differential scanning calorimeter is shifted to a low temperature side by 1 to 8° C. compared to an endothermic peak measured from mannitol only;

(26) the composition according to any one of the above (1) to (25), wherein a capping rate measured upon compression molding is 0.85 to 1.00;

(27) the composition according to any one of the above (1) to (25), wherein a capping rate measured upon compression molding is 0.90 to 1.00;

(28) the composition according to any one of the above (1) to (27), wherein an average particle diameter is 30 to 200 μm, a repose angle is 27 to 40°, and a static specific volume is 1.5 to 2.5 mL/g;

(29) the composition according to any one of the above (1) to (28), which is obtained by spray-drying an aqueous solution or an aqueous dispersion comprising components (a) to (c);

(30) the composition according to the above (29), which is obtained by spray-drying the dispersion obtained by dissolving or dispersing, in advance, mannitol and xylitol in an aqueous medium and then homogeneously dispersing the disintegrating agent and the inorganic excipient;

(31) the composition according to any one of the above (1) to (30), which further contains 0.01 to 100 parts by weight of a pharmacologically active ingredient and/or 0.01 to 1000 parts by weight of a component which does not deteriorate a disintegrating property based on 100 parts by weight of a total amount of mannitol, xylitol, the inorganic excipient and the disintegrating agent; and

(32) a rapid disintegrating tablet in oral cavity as prepared by using the composition according to any composition of the above (1) to (30), which comprises 0.01 to 100 parts by weight of a pharmacologically active ingredient and/or 0.01 to 1000 parts by weight of a component which does not deteriorate a disintegrating property, based on 100 parts by weight of the composition.

The term "rapid disintegrating tablet in oral cavity" used herein means a tablet which is able to be disintegrated in oral cavity rapidly, for example, within 40 seconds, preferably within 30 seconds, more preferably within 25 seconds and, still more preferably, within 20 seconds. The disintegration time in oral cavity used herein is the time which is measured by the measuring method mentioned in the Examples shown below.

DESCRIPTION OF THE PREFERRED EMBODIMENTS

Figure 1:
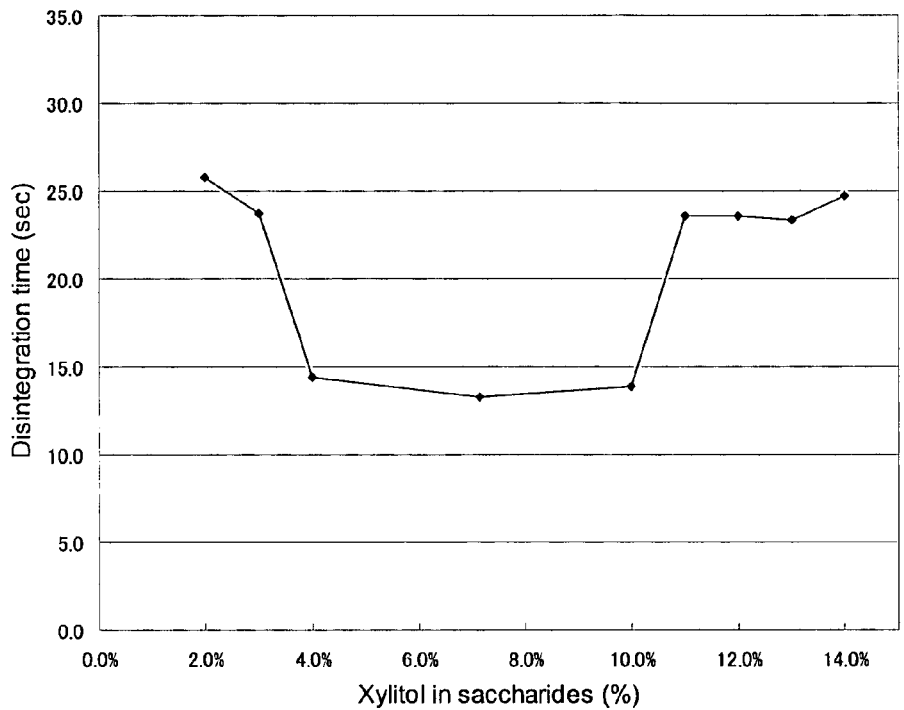
FIG. 1 is a graph where disintegration time in oral cavity is plotted relative to the ratio of xylitol in the saccharides (mannitol and xylitol), in accordance with the present invention.

With regard to saccharides (component (a)) comprised in the composition of the present invention, a mixture of mannitol and xylitol is used. This mixture forms complex particles. These saccharides are used in an amount of 40 to 90 parts by weight, preferably 50 to 80 parts by weight, more preferably 60 to 78 part by weight and, still more preferably, 62 to 78 parts by weight based on the total weight of the composition.

Ratio by weight of mannitol to xylitol as saccharides is preferably such that mannitol:xylitol=(98 to 67):(2 to 33), more preferably mannitol:xylitol=(98 to 87):(2 to 13), still more preferably mannitol:xylitol=(97 to 87:(3 to 13) and furthermore preferably mannitol:xylitol=(96 to 89):(4 to 11).

With regard to an average particle diameter of the saccharide used in the present invention, it is 500 μm or smaller, preferably 5 to 300 μm and, more preferably, 5 to 200 μm in order to preventing the roughness in oral cavity. However, since xylitol is always dissolved during the manufacture, one having any particle diameter may be used. Any mannitol and xylitol may be used so far as they are the substances commercially available.

Mannitol is usually used for obtaining powdery compositions having low hygroscopicity and high fluidity. However, its molding property is poor and its solubility is low as well and, therefore, when it is used in a composition for rapid disintegrating tablets, a balance between the disintegration time in oral cavity and the hardness of the resulting tablets has not been satisfactory.

However, the present inventors have found that, when mannitol is used in a specific ratio with xylitol, greatly shortened disintegration time in oral cavity, a good hardness and an excellent tablet-forming property may be obtained.

The inorganic excipient (component (b)) comprised in the composition of the present invention is used 1 to 30 part(s) by weight, preferably 2 to 20 parts by weight, more preferably 2 to 15 parts by weight, further preferably 2 to 9 parts by weight and, most preferably, 3 to 8 parts by weight based on the total weight of the composition; its average particle diameter is 0.1 to 100 µm, preferably, 1 to 60 µm and, more preferably, 1 to 40 µm.

The inorganic excipient preferably has an average pore diameter of 100 nm or smaller and is preferred to be a pharmaceutically acceptable inorganic compound containing any of aluminum, magnesium and calcium. It is preferably selected from, for example, magnesium aluminometasilicate, magnesium aluminosilicate, calcium hydrogen phosphate, hydrotalcite, synthetic aluminum silicate, calcium phosphate, calcium carbonate, talc, magnesium silicate, magnesium oxide, alumina-magnesium hydroxide, dry aluminum hydroxide gel, magnesium carbonate and calcium silicate; any of them may be used solely or in a mixture of two or more thereof. It is more preferably selected from magnesium aluminometasilicate, magnesium aluminosilicate, calcium hydrogen phosphate, hydrotalcite, calcium carbonate, calcium silicate, talc and dry aluminum hydroxide gel. It is still more preferably selected from magnesium aluminometasilicate, hydrotalcite, calcium hydrogen phosphate and calcium carbonate.

In the composition of the present invention, the disintegrating agent (component (c)) in the composition of the present invention is used 5 to 40 parts by weight, preferably 10 to 36 parts by weight, more preferably 16 to 35 parts by weight and, still more preferably, 18 to 34 parts by weight based on the total weight of the composition. Average particle diameter of the disintegrating agent is 0.1 to 100 µm, preferably 1 to 60 µm and, more preferably, 1 to 40 µm.

The disintegrating agent is preferably selected from crospovidone, low-substituted hydroxypropyl cellulose, croscarmellose sodium and crystalline cellulose and, although any of them may be used solely, it is preferred to use a mixture of two or more thereof. The disintegrating agent is preferably selected from crospovidone and crystalline cellulose and, although any of them may be used solely, it is preferred to use a mixture of both.

When crospovidone and crystalline cellulose are used as the disintegrating agent, crospovidone is contained, based on the total weight of the composition, preferably 5 to 15 parts by weight, more preferably 5 to 14 parts by weight and, still more preferably, 6 to 13 parts by weight, while crystalline cellulose is contained, based on the total weight of the composition, preferably 8 to 22 parts by weight, more preferably 10 to 22 parts by weight and, still more preferably, 12 to 21 parts by weight.

The composition of the present invention has such a structure that the disintegrating agent and the inorganic excipient are homogeneously dispersed in complex particles comprising mannitol and xylitol. As a result of making the composition into such a structure, the composition can have an improved disintegrating property and an excellent molding property as well.

The complex particles comprising mannitol and xylitol in the above composition include those which form a solid dispersion. The fact that the complex particles form a solid dispersion can be confirmed by the phenomenon that an endothermic peak of saccharides measured by a differential scanning calorimeter is shifted to a low temperature side. The complex particles are in such a state that xylitol molecule is substituted for mannitol molecule in a crystalline structure of mannitol or that xylitol molecule comes into pores of crystalline structure of mannitol causing a strain in the crystalline structure of mannitol whereupon a state of higher energy is resulted than normal crystals of mannitol only. Such a crystal has been known as a solid dispersion and, since it is more difficult to exist as solid than a pure substance, a phenomenon of depression of freezing point is resulted.

As a result of making mannitol into such a state of high energy, the composition of the present invention has now a high molding property, a rapid disintegrating property and a tablet hardness suitable as a composition for rapid disintegrating tablets in oral cavity even with mannitol which is usually poor in terms of a molding property, a rapid disintegrating property and a tablet hardness to be used as a composition for rapid disintegrating tablets in oral cavity.

Accordingly, it is preferred that shift of the endothermic peak of the saccharides to the low temperature side in the composition of the present invention is 0.5 to 19° C., more preferably 1 to 9° C. or, still more preferably, 1 to 8° C.; the composition as such has a good disintegration in oral cavity and a molding property upon tabletting. For the composition of the present invention, shift of the endothermic peak of the saccharides to a low temperature side is 0.5 to 19° C. when the ratio by weight of mannitol to xylitol is (98 to 67):(2 to 33), 1 to 9° C. when the ratio by weight of mannitol to xylitol is (97 to 87):(3 to 13) and 1 to 8° C. when the ratio by weight of mannitol to xylitol is (96 to 89):(4 to 11).

The composition of the present invention can be obtained as particles where the disintegrating agent and the inorganic excipient are homogeneously dispersed and that is a state in which the disintegrating agent and the inorganic excipient are not aggregated but are dispersed each other, and such a state is the optimum structure to introduce small amount of moisture in oral cavity into the tablet in a more abundant and more rapid manner. The state where the disintegrating agent and the inorganic excipient are dispersed can be observed under a scanning electron microscope. As a result of such measurement by the scanning electron microscope, each of the disintegrating agent and the inorganic excipient is dispersed in average particle diameter of 0.5 to 50 µm, preferably in 1 to 40 µm and, more preferably, in 2 to 30 µm. It is believed that water-introducible pores of the specific inorganic excipient introduce small amount of water into the tablet and the water effectively act on the disintegrating agent which is also dispersed, thus a favorable rapid disintegration in oral cavity is obtained.

The composition of the present invention is characterized that a compression property on a common rotary tablet machine is good in spite of a high compounding rate of saccharides. The fact that the compression property is good is shown by means of a capping rate which is measured by a tabletting tester. The capping rate of the present composition is 0.85 to 1.00 or, preferably, 0.90 to 1.00. The capping rate is able to be measured by tabletting 400 to 500 mg of the composition using a tabletting tester (SK-02 manufactured by Sankyo Pio-Tech Co., Ltd.) under the conditions of 500 to 1,000 kg/cm$^2$ of compressing pressure using a punch of 11.3 mm.

With regard to common troubles upon tabletting a composition containing saccharides, it has been also known that troubles of not only capping but also sticking, die friction (binding), etc. are apt to happen. However, even when the present composition is subjected to a high-speed compression (50 to 60 rpm) using a rotary tablet machine, there is generated no troubles in tabletting such as capping, sticking and die friction.

Besides the saccharides, the inorganic excipient and the disintegrating agent, the composition of the present invention may be compounded with a pharmacologically active ingredient and/or a component which does not deteriorate the disintegrating property.

The pharmacologically active ingredient is able to be compounded in an amount of 0.01 to 100 part(s) by weight, preferably 0.01 to 67 part(s) by weight or, more preferably, 0.01 to 60 part(s) by weight based on 100 parts by weight of the total amount of the saccharides, the disintegrating agent and the inorganic excipient.

The composition of the present invention is able to be produced by compounding the pharmacologically active ingredient with the saccharides, the inorganic excipient and the disintegrating agent.

The component which does not deteriorate the disintegrating property is able to be compounded in an amount of 0.01 to 1000 part(s) by weight or, preferably, in 0.1 to 500 part(s) by weight based on 100 parts by weight of the total amount of the saccharides, the disintegrating agent and the inorganic excipient. The composition of the present invention is able to be produced by compounding the component which does not deteriorate the disintegrating property with the saccharides, the inorganic excipient and the disintegrating agent.

The composition of the present invention may be prepared by any manufacturing method so long as a desired physical property can be achieved by the component ratio of the composition of the present invention although, preferably, it is prepared by a spray-drying method.

The particles having a characteristic structure of the present invention where the disintegrating agent and the inorganic excipient are homogeneously dispersed in a complex particle formed from mannitol and xylitol can be easily prepared by means of the spray-drying method.

The composition of the present invention is able to be produced by spray-drying an aqueous solution or an aqueous dispersion containing the components (a) to (c) according to a common method. More specifically, it is able to be produced in such a manner that mannitol and xylitol are dissolved or dispersed in advance in an aqueous medium, the disintegrating agent and the inorganic excipient are homogeneously dispersed therein and the resulting dispersion is spray-dried. The expression reading "mannitol and xylitol are dissolved or dispersed in advance in an aqueous medium" means the following. Thus, it is sufficient that at least a part of mannitol and at least a part of xylitol are dissolved in the aqueous medium and that remaining parts of mannitol and xylitol may be either dissolved or dispersed. For the purpose that mannitol and xylitol form a solid dispersion, it is preferred that a part of mannitol and all of xylitol are dissolved therein.

With regard to the above-mentioned aqueous medium, any medium may be used so far as it has no affects on the physical property of the composition and which is pharmaceutically acceptable, examples thereof being water, ethanol and methanol.

To the dispersion, a pharmacologically active ingredient may be optionally added and a component which does not deteriorate the disintegrating property may be optionally added. The aqueous dispersion may be prepared by a known method and, although common methods such as stirring method, colloid mill method, high-pressure homogenizer method and ultrasonic wave irradiation method may be exemplified, a method in which the particles are highly dispersed in an aqueous dispersion is preferred. It is particularly preferred that xylitol is completely dissolved, all or a part of mannitol is dissolved and water-insoluble substances, e.g. crospovidone, crystalline cellulose and inorganic excipient are disintegrated in a solution whereupon the dispersion having a high dispersing property is prepared. With regard to a solid concentration of the dispersion, it may be within a range by which spray-drying is able to be conducted; and it is usually 10 to 50% by weight or, preferably, 25 to 45% by weight.

There is no particular limitation for the condition of spray-drying. However, with regard to a spray-dryer, it is preferred to use a spray-dryer of a disk type or a nozzle type. With regard to the temperature for spray-drying, it is preferred that the inlet temperature is about 120 to 220° C. and the outlet temperature is about 80 to 130° C. With regard to the solid concentration of the aqueous dispersion upon spray-drying, it may be within a range by which the spray-drying is able to be conducted and it is usually 10 to 50% by weight and, preferably, it is 25 to 45% by weight.

Average particle diameter of the composition of the present invention prepared as such can be appropriately adjusted depending upon concentration of the aqueous solution or aqueous dispersion, spray-drying method, drying condition, etc. and, when it is 1 to 500 μm, preferably 5 to 300 μm, more preferably 10 to 200 μm or, still more preferably, 30 to 200 μm, a rough feeling in oral cavity can be prevented whereby that is preferred.

A static specific volume of the above composition is preferably about 1.5 to 4.0 g/ml, more preferably about 1.5 to 3.5 g/ml and, still more preferably, about 1.5 to 2.5 g/ml. Due to such a static specific volume, it is easy to fill the composition in a die upon tabletting and, therefore, a step for manufacturing of the tablets proceeds smoothly and, in addition, tablets are able to be uniformly compressed showing an excellent tabletting property. The static specific volume can be measured by a standard method.

Repose angle of the composition is 20 to 45° and, preferably 27 to 40°. Because the composition has such a repose angle, it shows an excellent fluidity and shows an excellent tabletting property in the manufacturing process. The repose angle is able to be measured according to a standard method by using a powder tester (manufactured by Hosokawamicron Corp.).

The rapid disintegrating tablets in oral cavity according to the present invention is one obtained by compounding 0.01 to 100 part(s) by weight, preferably 0.01 to 67 part(s) by weight or, more preferably, 0.1 to 60 part(s) by weight of a pharmacologically active ingredient and 0.01 to 1000 part(s) by weight or, preferably, 0.1 to 100 part(s) by weight of a component which does not deteriorate a disintegrating property, based on 100 parts by weight of the composition prepared as mentioned above. With regard to the pharmacologically active ingredient, one which is coated by a known method may be used when it has bitter taste; it may also be subjected for controlled release by a known method for effecting release thereof in digestive tracts.

With regard to the pharmacologically active ingredient used in the present invention, any forms such as solid, crystal, oil and solution may be used. There is no particular limitation for the use and one or more ingredient(s) selected from the followings is/are used; for example, central nerve system acting drugs such as agent for peripheral nerve, antipyretic/analgesic/anti-inflammatory agent, hypnotic/analgesic agent, agent for psychological nerve, psychotropic agent, antianxiety agent, antidepressant, hypnotic/analgesic agent, antiepileptic agent, sympathomimetic agent and antispasmodic; drugs for peripheral nerve such as skeletal muscle relaxant and autonomic agent; drugs for circulatory organs such as bronchodilator, cardiotonic, agent for arrhythmia, diuretic, respiratory stimulant and vasodilator; drugs for respiratory organs such as bronchodilator and antitussive; pharmaceuticals for digestive tracts such as digestive, antiflatuent, antiulcer agent and antacid; metabolic drugs such as brain metabolic stimulant, hormone preparation, anti-histaminic agent and vitamin preparation; antiulcer agent; antibiotic; chemotherapeutic; extract of traditional oriental medicines; nutritional and tonic medicine; medicine for allergy; and microbes.

As the pharmacologically active ingredient, active ingredients of cold medicine and active ingredient for rhinitis may also be mentioned. Examples of the active ingredient of cold medicine include antipyretic/analgesic/anti-inflammatory agent, bronchodilator, antihistaminic agent, antitussive agent, expectorant, antitussive/expectorant, vitamin preparation and extract of traditional Chinese medicines. Examples of the active ingredient for rhinitis include sympathetic stimulant, parasympatholytic agent, anti-allergic agent and anti-inflammatory agent.

Examples of the antipyretic/analgesic/anti-inflammatory agent include aniline derivatives such as acetaminophen, phenacetin and lefetamine hydrochloride; salicylic acid derivatives such as ethenzamide, sasapyrine, methyl salicylate, phenyl salicylate, sodium salicylate, choline salicylate, aspirin and aluminum aspirin; pyrazolone derivatives such as isopropylantipyrine, sulpyrine, phenylbutazone, ketodphenylbutazone, antipyrine and aminopyridine; propionic acid derivatives such as ibuprofen, ketoprofen, oxaprozin, naproxen, calcium fenoprofen and tiaprofenic acid; phenylacetic acid derivatives such as fenbufen, diclofenac sodium and amfenac sodium; indoleacetic acid derivatives such as indomethacin, indomethacin farnesil, proglumetacin maleate and tolmetin sodium; anthranylacetic acid derivatives such as mefenamic acid, fluphenamic acid and tolfenamic acid; oxicam derivatives such as piroxicam, ampiroxicam and tenoxicam; benzidamine hydrochloride; epirizole (mepirizole), tinoridine hydrochloride; tiaramide hydrochloride; anti-inflammatory enzyme preparation; Serapeptidase (trade name); and lysozyme chloride. These antipyretic/analgesic/anti-inflammatory agents may be used solely or two or more thereof may be used jointly.

Examples of the bronchodilator include ephedrine hydrochloride, dl-methylephedrine hydrochloride, dl-methylephedrine hydrochloride saccharinate, isoprenaline hydrochloride, isoproterenol sulfate, methoxyphenamine hydrochloride, orciprenaline sulfate, chlorprenaline hydrochloride, trimetoquinol hydrochloride, salbutamol sulfate, terbutaline sulfate, hexoprenaline sulfate, formoterol fumarate, fenoterol hydrobromide, procaterol hydrochloride, clenbuterol hydrochloride, mabuterol hydrochloride, xanthine derivatives such as aminophylline, theophylline, diprophylline and proxyphylline and anticholinergic agent such as flutropium bromide and oxitropium bromide.

Examples of the anti-histaminic agent are antihistaminic agent of an ethanolamine type such as diphenhydramine, antihistaminic agent of a propylamine type such as dl-chlorpheniramine maleate and d-chlorpheniramine maleate, antihistaminic agent of a phenothiazine type such as alimemazine tartrate, isothipendyl hydrochloride, promethazine hydrochloride and mequitazine, diphenylpyraline, carbinoxamine maleate, clemastine fumarate, iproheptine hydrochloride, homochlorcyclizine hydrochloride, cyproheptadine hydrochloride, dimethindene maleate and triprolidine hydrochloride.

Examples of the antitussive agent include codeines such as codeine phosphate and dihydrocodeine phosphate, dextromethorphan hydrobromide, cloperastine, noscapine dimemorfan, oxeladin, pentoxiverin citrate, eprazinone hydrochloride, clobutinol hydrochloride, isoaminile citrate, fominoben hydrochloride, clofedanol hydrochloride, benproperine phosphate, hydrocotarnine and dibunate sodium.

Examples of the expectorant include potassium guiacolsulfonate, cysteine derivatives such as carbocysteine, L-ethylcysteine hydrochloride, L-methylcysteine hydrochloride and acetylcysteine, bromhexine and ambroxol hydrochloride. Examples of the antitussive/expectorant include guaifenesin, tipepidine, oxymethebanol, alloclamide hydrochloride, carbetapentane phenate, trimethoquinol hydrochloride and methoxyphenamine hydrochloride. Incidentally, the pharmacologically active ingredients which are exemplified hereinabove as antitussive, expectorant and antitussive/expectorant sometimes exhibit antitussive action and/or expectorant action in a complexed manner.

Examples of the psychotropic agent include chlorpromazine and reserpine. Examples of the anti-anxiety agent include alprazolam, chlordiazepoxide and diazepam. Examples of the antidepressant include maprotiline hydrochloride, imipramine, and amphetamine. Examples of the hypnotic/sedative agent include estazolam, nitrazepam, diazepam, perlapin and phenobarbital sodium. Examples of the antispasmodic agent include scopolamine hydrobromide, papaverine hydrochloride and diphenhydramine hydrochloride. Examples of agent acting on central nerve include citicoline, etc. Examples of the anti-epileptic agent include phenytoin and carbamazepine. Examples of the sympathomimetic agent include isoproterenol hydrochloride, etc.

The gastrointestinal drug includes, for example, digestant such as diastase, saccharated pepsin, scopolia extract, cellulose AP3, lipase AP and cinnamon bark oil and antiflatuent such as berberine chloride, Lactobacillus and Bifidobacterium. Examples of the antacid include magnesium carbonate, sodium hydrogen carbonate, magnesium aluminometasilicate, magnesium aluminosilicate, synthetic hydrotalcite, precipitated calcium carbonate and magnesium oxide. Examples of the antiulcer agent include famotidine, lansoprazole, omeprazole, rabeprazole, cimetidine and ranitidine hydrochloride.

Examples of the cardiotonic agent include caffeine and digoxin. Examples of the anti-arrhythmic agent include procainamide hydrochloride, propranolol hydrochloride and pindolol. Examples of the diuretic agent include isosorbide, furosemide and hydrochlorothiazide. Examples of the hypotensive agent include delapril hydrochloride, captopril, hydralazine hydrochloride, labetalol hydrochloride, manidipine hydrochloride, candesartan cilexetil, methyldopa and perindopril erbumine. Examples of angiotonic include phenylephrine hydrochloride, etc. Examples of coronary vasodilator include carbocromen hydrochloride, molsidomine and verapamil hydrochloride. Examples of the peripheral blood vessel dilator include cinnarizine, etc.

Examples of the agent for hyperlipemia include cerivastatin sodium, simvastatin, pravastatin sodium and atorvastatin calcium hydrate.

Examples of the antibiotic include cephem antibiotics such as cephalexin, cefaclor, amoxicillin, pivmecillinam hydrochloride, cefotiam hexetil hydrochloride, cefadroxil, cefixime, cefditoren pivoxil, cefteram pivoxil and cefpodoxime proxetil; synthetic antibiotics such as ampicillin, ciclacillin, nalidixic acid and enoxacin; monobactam antibiotics such as carumonam sodium; penem antibiotics; and carbapenem antibiotics.

Examples of the chemotherapeutic include sulfamethizole, etc.

Examples of the antidiabetic agent include tolbutamide, voglibose, pioglitazone hydrochloride, glibenclamide and troglitazone.

Examples of the antispasmodic agent include meclizine hydrochloride and dimenhydrinate.

Examples of the anti-rheumatic agent include methotrexate and bucillamine.

Examples of the hormone preparation include liothyronine sodium, dexamethasone sodium phosphate, prednisolone, oxendolone and leuprorelin acetate.

Examples of the alkaloidal narcotic include opium, morphine hydrochloride, thoron, oxycodone hydrochloride, opium alkaloid hydrochloride and cocaine hydrochloride.

Examples of the sulfa drug include sulfisomidine and sulfamethizole.

Examples of the drug for treatment of gout include allopurinol and cholchicine.

Examples of the anticoagulant include dicumarol, etc.

Examples of the agent for malignant tumor include 5-fluorouracil, uracil, mitomycin, manidipine hydrochloride, voglibose, candesartan cilexetil and pioglitazone hydrochloride.

Examples of vitamin preparation include carotenoid such as astaxanthin, vitamin A, β-carotene, lutein and zeaxanthin; vitamin B1 or derivative thereof or salt thereof such as fursultiamine, fursultiamine hydrochloride, prosultiamine, octotiamine, thiamine disulfide, bisbentiamine, bisbutytiamine, bisibutiamine, benfotiamine and cetotiamine hydrochloride; vitamin B2 or derivative thereof or salt thereof such as riboflavin, riboflavin sodium phosphate, flavin adenine dinucleotide sodium and riboflavin butyrate; vitamin C derivative such as ascorbic acid, ascorbic acid glucoside, L-ascorbyl palmitate and L-ascorbic acid phosphate; vitamin E such as tocopherol, tocopherol acetate, tocopherol succinate, tocopherol nicotinate and tocotrienol; etc.

Depending upon the type of the pharmacologically active ingredient used, there is a possibility that the range of amount of the component comprised in the composition of the present invention capable of providing a favorable rapid disintegrating property in oral cavity varies and such variation is also within a scope of the present invention.

The rapid disintegrating tablets in oral cavity according to the present invention can be prepared by compression molding of a mixture in which the above-mentioned composition is compounded with the pharmacologically active ingredient and the component which does not deteriorate the disintegrating property. It is preferred that the compression molding is carried out by a direct tabletting method.

The component which does not deteriorate the disintegrating property and which can be added to the composition of the present invention and/or to the rapid disintegrating tablets in oral cavity of the present invention includes excipient (e.g. carboxymethylcellulose calcium, hydrogenated oil and talc), surfactant (e.g. polyoxyethylene hydrogenated castor oil, polyoxyethylene polyoxypropylene glycol, sorbitan fatty acid ester, polysorvate, fatty acid glycerol ester and sodium lauryl sulfate), binder (e.g. hydroxypropyl cellulose, alginic acid, gelatin, partial pregelatinized starch, povidone, gum acacia, pullulan and dextrin), lubricant (e.g. stearic acid, magnesium stearate, calcium stearate, sucrose fatty acid ester, polyethylene glycol and stearyl fumarate sodium), acidifier (e.g. citric acid, tartaric acid, malic acid and ascorbic acid), foaming agent (e.g. sodium hydrogen carbonate and sodium carbonate), sweetener (e.g. saccharine sodium, dipotassium glycyrrhizin, aspartame, stevia and thaumatin), flavor (e.g. lemon oil, orange oil and menthol), coloring agent (e.g. food dye Red No. 2, food dye Blue No. 2, food dye Yellow No. 5, lake dye for food and iron sesquioxide), stabilizer (e.g. sodium edetate, tocopherol and cyclodextrin), corrigent and flavoring agent. These components may be added to such an extent that they do not deteriorate the rapid disintegrating property of the tablets of the present invention.

The rapid disintegrating tablets in oral cavity according to the present invention have a hardness of preferably 2 to 20 kg, more preferably 2 to 15 kg and, still more preferably, 3 to 12 kg. Tabletting pressure varies according to the size of the tablet and, when tablets each weighing 200 mg are prepared by compression using, for example, a punch of 8 mm diameter, the hardness is 2 to 15 kg in case the tabletting pressure is 100 to 1200 kgf and is 3 to 7 kg in case the tabletting pressure is 200 to 800 kgf.

EXAMPLES

The present invention will now be illustrated by way of the following Examples although they are not intended to limit the scope of the present invention.

Evaluation of each tablet prepared in the Examples was carried out according to the following methods.

Disintegration Time in Oral Cavity

The time from when tablets (six tablets) were placed in oral cavity of 3 to 8 panelists until they were completely disintegrated was measured and its mean value was adopted as a disintegration time in oral cavity.

Hardness of Tablets

Measurement was conducted using a Monsanto hardness meter (manufactured by Kayagaki Irika Kogyo).

Troubles upon Tabletting

It was observed whether there are adhered matters to upper and lower punches of a tablet machine (sticking, capping and die friction) to evaluate the tabletting troubles.

Example 1

Xylitol (50 g) was completely dissolved in 1500 mL of water, 650 g of mannitol was then added and the mixture was stirred at room temperature at 200 to 300 rpm for 60 minutes using a wet dispersing device (Mycolloider type M; manufactured by Tokushu Kika Kogyo Co., Ltd.) to give a dispersion in which mannitol was homogeneously dispersed. To the dispersion were added 80 g of crospovidone, 150 g of crystalline cellulose and 70 g of magnesium aluminometasilicate (Neusilin UFL2; manufactured by Fuji Chemical Industry Co., Ltd.) and, after the mixture was homogeneously dispersed, it was spray-dried using a spray-dryer (type L-8; manufactured by Okawahara Kakohki Co., Ltd.) to give a composition (Example 1-4).

The resulting composition (500 parts by weight) was mixed with 2.5 parts by weight of magnesium stearate and compression-molded using a rotary tablet machine (HT-AP18SS-II; manufactured by Hata Iron Works Co., Ltd.) to prepare tablets each weighing 200 mg and having a diameter of 8 mm.

By the same method as above, tablets were obtained by using the same method as mentioned above except that the ratio of mannitol to xylitol was changed as shown in Table 1.

Disintegration time in oral cavity of the resulting tablets was measured (n=6). The result is shown in Table 1. The graph where the disintegration time in oral cavity was plotted to the ratio of xylitol in the saccharides (mannitol and xylitol) is shown in FIG. 1.

TABLE 1

|  |  | \multicolumn{9}{c}{Examples} |
| --- | --- | --- | --- | --- | --- | --- | --- | --- | --- | --- |
|  |  | 1-1 | 1-2 | 1-3 | 1-4 | 1-5 | 1-6 | 1-7 | 1-8 | 1-9 |
| Formulation (g) | Mannitol | 686.0 | 679.0 | 672.0 | 650.0 | 630.0 | 623.0 | 616.0 | 609.0 | 602.0 |
|  | Xylitol | 14.0 | 21.0 | 28.0 | 50.0 | 70.0 | 77.0 | 84.0 | 91.0 | 98.0 |
|  | Xylitol in saccharides | 2% | 3% | 4% | 7% | 10% | 11% | 12% | 13% | 14% |
|  | Crystalline cellulose | 150.0 | 150.0 | 150.0 | 150.0 | 150.0 | 150.0 | 150.0 | 150.0 | 150.0 |
|  | Crospovidone | 80.0 | 80.0 | 80.0 | 80.0 | 80.0 | 80.0 | 80.0 | 80.0 | 80.0 |
|  | Mg aluminometasilicate | 70.0 | 70.0 | 70.0 | 70.0 | 70.0 | 70.0 | 70.0 | 70.0 | 70.0 |
|  | Total | 1000.0 | 1000.0 | 1000.0 | 1000.0 | 1000.0 | 1000.0 | 1000.0 | 1000.0 | 1000.0 |
| Disintegration time in oral cavity (sec) |  | 25.8 | 23.7 | 14.4 | 13.2 | 13.9 | 23.6 | 23.6 | 23.3 | 25.7 |

From the result of Table 1, it is noted that, in a composition containing mannitol, xylitol, crystalline cellulose, crospovidone and magnesium aluminometasilicate, the disintegration time in oral cavity of the resulting tablet prepared from the composition is good when the ratio of xylitol in the saccharides is 3 to 13% by weight, it is better when the ratio of xylitol in the saccharides is 3 to 11% by weight and it is particularly good when the ratio of xylitol in the saccharides is 4 to 10% by weight.

Example 2

Figure 2:
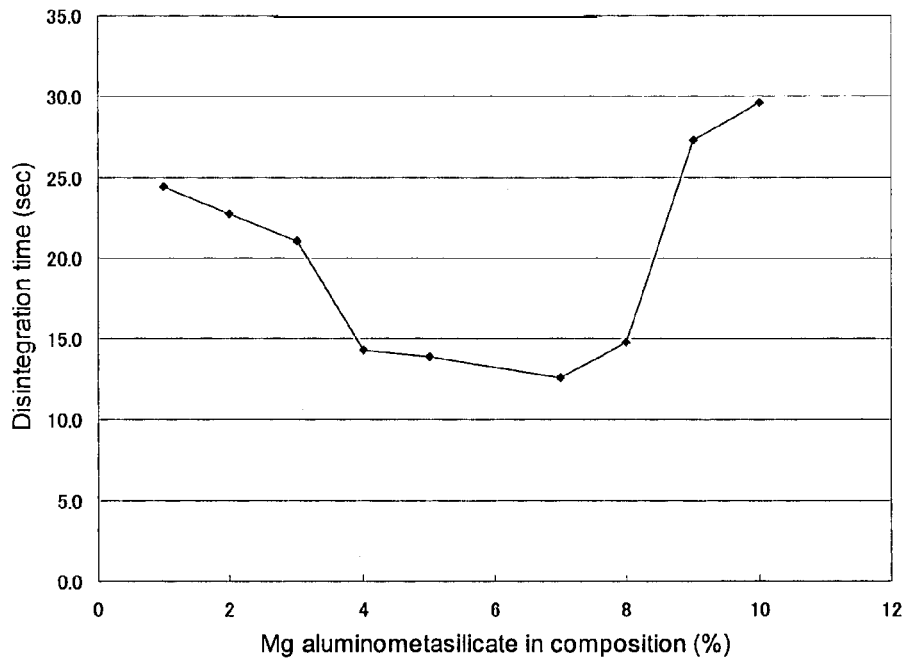
FIG. 2 is a graph where disintegration time in oral cavity is plotted relative to the ratio of magnesium aluminometasilicate in the composition of the present invention.

Compositions and tablets were prepared using the formulations shown in Table 2 by the same manner as in Example 1. Disintegration time in oral cavity of the resulting tablets was measured (n=6). The result is shown in Table 2. The graph where the disintegration time in oral cavity was plotted to the amount of magnesium aluminometasilicate in the composition is shown in FIG. 2.

From the result of Table 2, it is noted that, in a composition containing mannitol, xylitol, crystalline cellulose, crospovidone and magnesium aluminometasilicate, the disintegration time in oral cavity of the resulting tablet is good when the ratio of magnesium aluminometasilicate in the composition is 1 to 9 parts by weight, that it is better when the ratio of magnesium aluminometasilicate in the composition is 3 to 9 parts by weight and that it is particularly good when the ratio of magnesium aluminometasilicate in the composition is 4 to 8 parts by weight.

Example 3

Figure 3:
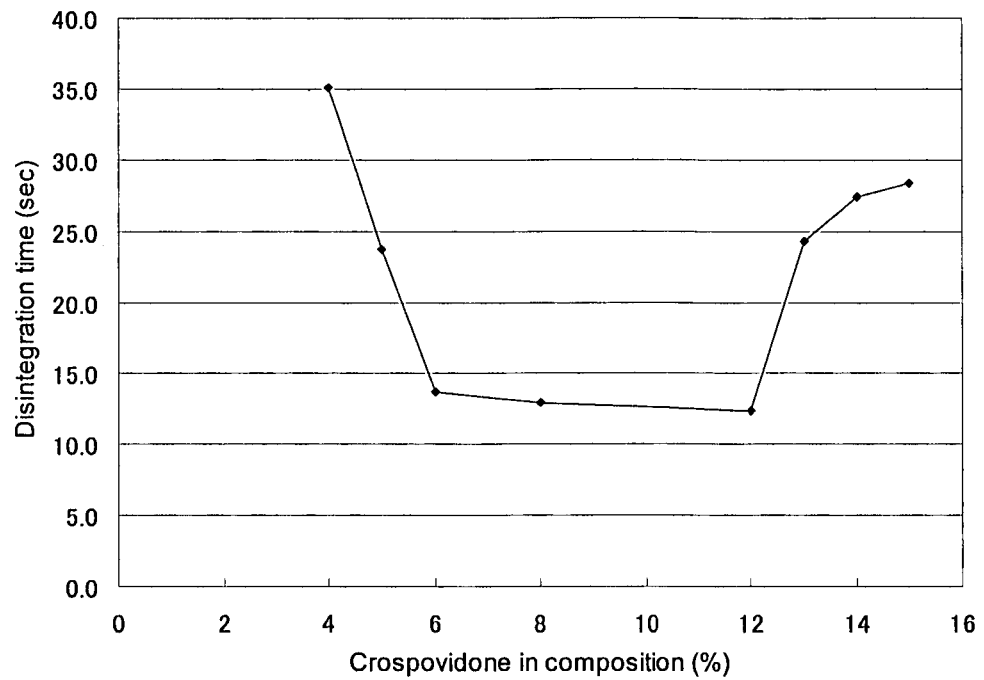
FIG. 3 is a graph where disintegration time in oral cavity is plotted relative to the ratio of crospovidone in the composition of the present invention.

Compositions and tablets were prepared using the formulations shown in Table 3 by the same manner as in Example 1. The disintegration time in oral cavity of the resulting tablets was measured (n=6). The result is shown in Table 3. The graph where the disintegration time in oral cavity was plotted to the amount of crospovidone in the composition is shown in FIG. 3.

TABLE 2

|  |  | \multicolumn{9}{c}{Examples} |
| --- | --- | --- | --- | --- | --- | --- | --- | --- | --- | --- |
|  |  | 2-1 | 2-2 | 2-3 | 2-4 | 2-5 | 2-6 | 2-7 | 2-8 | 2-9 |
| Formulation (g) | Mannitol | 705.5 | 696.4 | 687.1 | 677.9 | 668.6 | 650.0 | 640.7 | 631.5 | 622.0 |
|  | Xylitol | 54.5 | 53.6 | 52.9 | 52.1 | 51.4 | 50.0 | 49.3 | 48.5 | 48.0 |
|  | Crystalline cellulose | 150.0 | 150.0 | 150.0 | 150.0 | 150.0 | 150.0 | 150.0 | 150.0 | 150.0 |
|  | Crospovidone | 80.0 | 80.0 | 80.0 | 80.0 | 80.0 | 80.0 | 80.0 | 80.0 | 80.0 |
|  | Mg aluminometasilicate | 10.0 | 20.0 | 30.0 | 40.0 | 50.0 | 70.0 | 80.0 | 90.0 | 100.0 |
|  | Total | 1000.0 | 1000.0 | 1000.0 | 1000.0 | 1000.0 | 1000.0 | 1000.0 | 1000.0 | 1000.0 |
| Disintegration time in oral cavity (sec) |  | 24.4 | 22.7 | 21.0 | 14.3 | 13.9 | 12.6 | 14.8 | 27.3 | 29.7 |

TABLE 3

|  |  | Examples | | | | | | | |
|---|---|---|---|---|---|---|---|---|---|
|  |  | 3-1 | 3-2 | 3-3 | 3-4 | 3-5 | 3-6 | 3-7 | 3-8 |
| Formulation (g) | Mannitol | 687.0 | 677.9 | 668.6 | 650.0 | 612.9 | 603.6 | 594.3 | 585.0 |
|  | Xylitol | 53.0 | 52.1 | 51.4 | 50.0 | 47.1 | 46.4 | 45.7 | 45.0 |
|  | Crystalline cellulose | 150.0 | 150.0 | 150.0 | 150.0 | 150.0 | 150.0 | 150.0 | 150.0 |
|  | Crospovidone | 40.0 | 50.0 | 60.0 | 80.0 | 120.0 | 130.0 | 140.0 | 150.0 |
|  | Mg aluminometasilicate | 70.0 | 70.0 | 70.0 | 70.0 | 70.0 | 70.0 | 70.0 | 70.0 |
|  | Total | 1000.0 | 1000.0 | 1000.0 | 1000.0 | 1000.0 | 1000.0 | 1000.0 | 1000.0 |
| Disintegration time in oral cavity (sec) |  | 35.1 | 23.7 | 13.7 | 12.9 | 12.4 | 24.3 | 27.5 | 28.3 |

From the result of Table 3, it is noted that, in a composition containing mannitol, xylitol, crystalline cellulose, crospovidone and magnesium aluminometasilicate, the disintegration time in oral cavity of the resulting tablet is good when the ratio of crospovidone in the composition is 5 to 13 parts by weight and that it is particularly good when the ratio of crospovidone in the composition is 6 to 12 parts by weight.

Example 4

Figure 4:
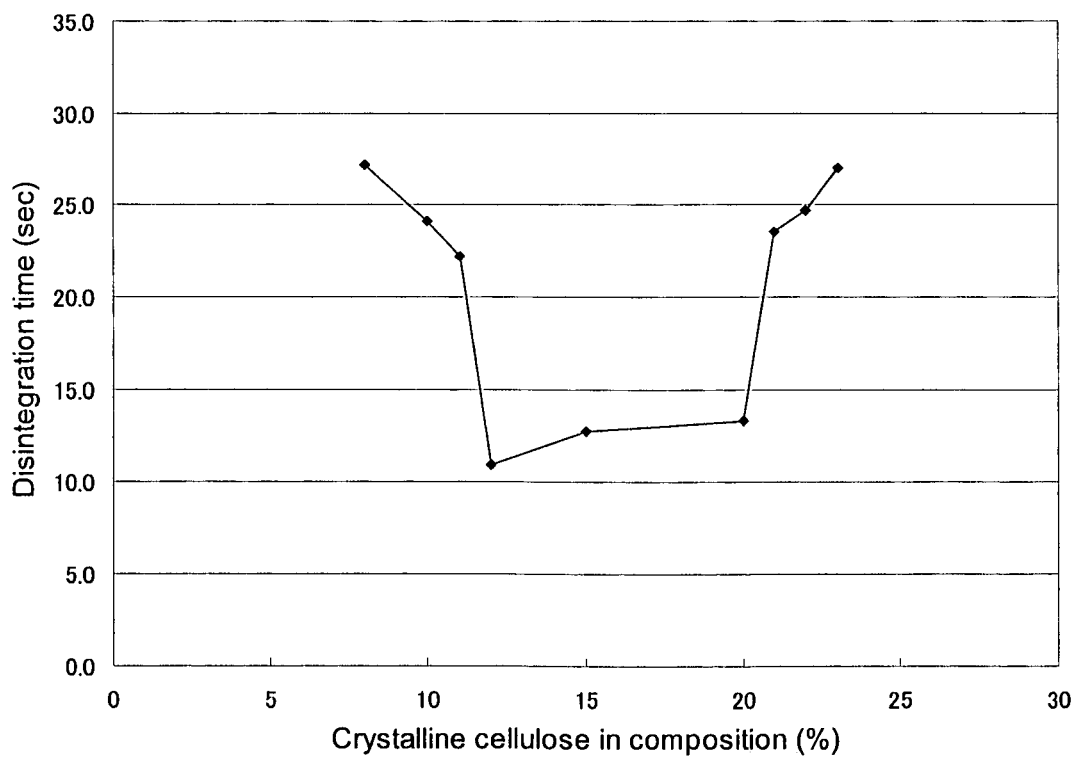
FIG. 4 is a graph where disintegration time in oral cavity is plotted relative to the ratio of crystalline cellulose in the composition of the present invention.

Compositions and tablets were prepared using the formulations shown in Table 4 by the same manner as in Example 1. The disintegration time in oral cavity of the resulting tablets was measured (n=6). The result is shown in Table 4. The graph where the disintegration time in oral cavity was plotted to the amount of crystalline cellulose in the composition is shown in FIG. 4.

From the result of Table 4, it is noted that, in a composition containing mannitol, xylitol, crystalline cellulose, crospovidone and magnesium aluminometasilicate, the disintegration time in oral cavity of the resulting tablet is good when the ratio of crystalline cellulose in the composition is 10 to 22 parts by weight, that it is better when the ratio of crystalline cellulose in the composition is 11 to 21 parts by weight and that it is particularly good when the ratio of crystalline cellulose in the composition is 12 to 20 parts by weight.

Example 5

Figure 5:
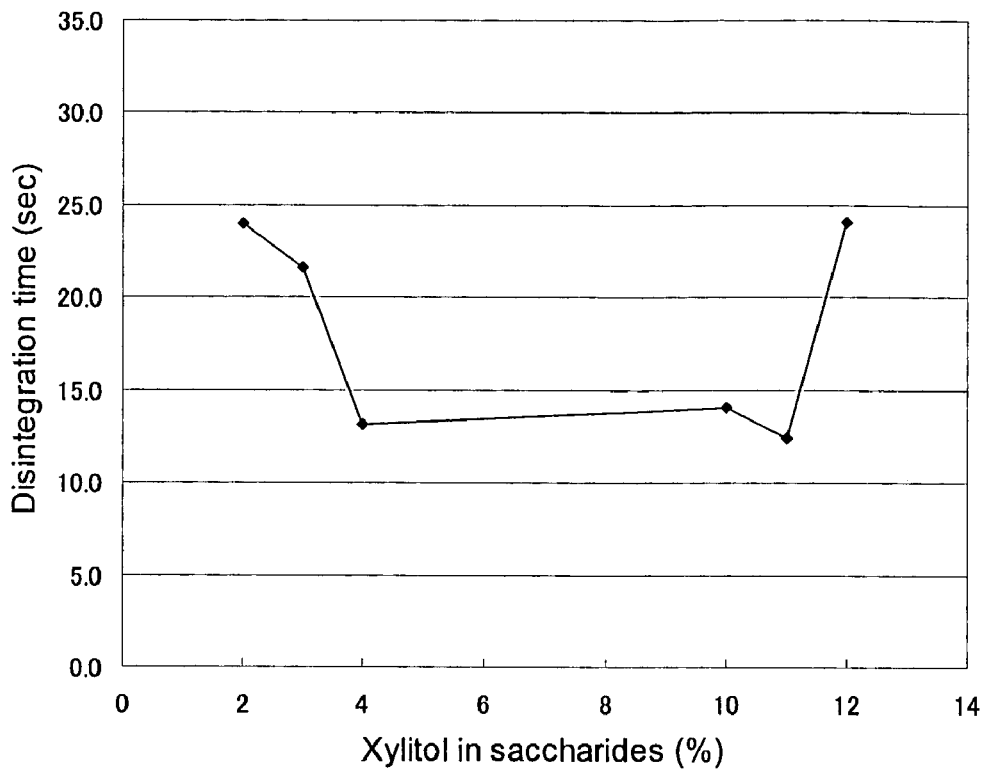
FIG. 5 is a graph where disintegration time in oral cavity is plotted relative to the ratio of xylitol in the saccharides (mannitol and xylitol), in accordance with the present invention.

Compositions and tablets were prepared using the formulations shown in Table 5 by the same manner as in Example 1. The disintegration time in oral cavity of the resulting tablets was measured (n=6). The result is shown in Table 5. The graph where the disintegration time in oral cavity was plotted to the amount of xylitol in the saccharides (mannitol and xylitol) is shown in FIG. 5.

TABLE 4

|  |  | Examples | | | | | | | | |
|---|---|---|---|---|---|---|---|---|---|---|
|  |  | 4-1 | 4-2 | 4-3 | 4-4 | 4-5 | 4-6 | 4-7 | 4-8 | 4-9 |
| Formulation (g) | Mannitol | 715.0 | 696.5 | 687.1 | 677.9 | 650.0 | 603.6 | 594.3 | 585.0 | 575.5 |
|  | Xylitol | 55.0 | 53.5 | 52.9 | 52.1 | 50.0 | 46.4 | 45.7 | 45.0 | 44.5 |
|  | Crystalline cellulose | 80.0 | 100.0 | 110.0 | 120.0 | 150.0 | 200.0 | 210.0 | 220.0 | 230.0 |
|  | Crospovidone | 80.0 | 80.0 | 80.0 | 80.0 | 80.0 | 80.0 | 80.0 | 80.0 | 80.0 |
|  | Mg aluminometasilicate | 70.0 | 70.0 | 70.0 | 70.0 | 70.0 | 70.0 | 70.0 | 70.0 | 70.0 |
|  | Total | 1000.0 | 1000.0 | 1000.0 | 1000.0 | 1000.0 | 1000.0 | 1000.0 | 1000.0 | 1000.0 |
| Disintegration time in oral cavity (sec) |  | 27.2 | 24.1 | 22.2 | 10.9 | 12.7 | 13.3 | 23.5 | 24.7 | 27.1 |

TABLE 5

| | | Examples | | | | | |
| --- | --- | --- | --- | --- | --- | --- | --- |
| | | 5-1 | 5-2 | 5-3 | 5-4 | 5-5 | 5-6 |
| Formulation (g) | Mannitol | 686.0 | 679.0 | 672.0 | 630.0 | 623.0 | 616.0 |
| | Xylitol | 14.0 | 21.0 | 28.0 | 70.0 | 77.0 | 84.0 |
| | Xylitol in saccharides | 2% | 3% | 4% | 10% | 11% | 12% |
| | Crystalline cellulose | 180.0 | 180.0 | 180.0 | 180.0 | 180.0 | 180.0 |
| | Crospovidone | 80.0 | 80.0 | 80.0 | 80.0 | 80.0 | 80.0 |
| | Ca hydrogen phosphate | 40.0 | 40.0 | 40.0 | 40.0 | 40.0 | 40.0 |
| | Total | 1000.0 | 1000.0 | 1000.0 | 1000.0 | 1000.0 | 1000.0 |
| | Disintegration time in oral cavity (sec) | 24.0 | 21.6 | 13.1 | 14.0 | 12.4 | 24.1 |

From the result of Table 5, it is noted that, in a composition containing mannitol, xylitol, crystalline cellulose, crospovidone and calcium hydrogen phosphate, the disintegration time in oral cavity of the resulting tablet is good when the ratio of xylitol in the saccharides is 2 to 12% by weight, that it is better when the ratio of xylitol in the saccharides is 3 to 12% by weight and that it is particularly good when the ratio of xylitol in the saccharides is 4 to 11% by weight.

Example 6

Figure 6:
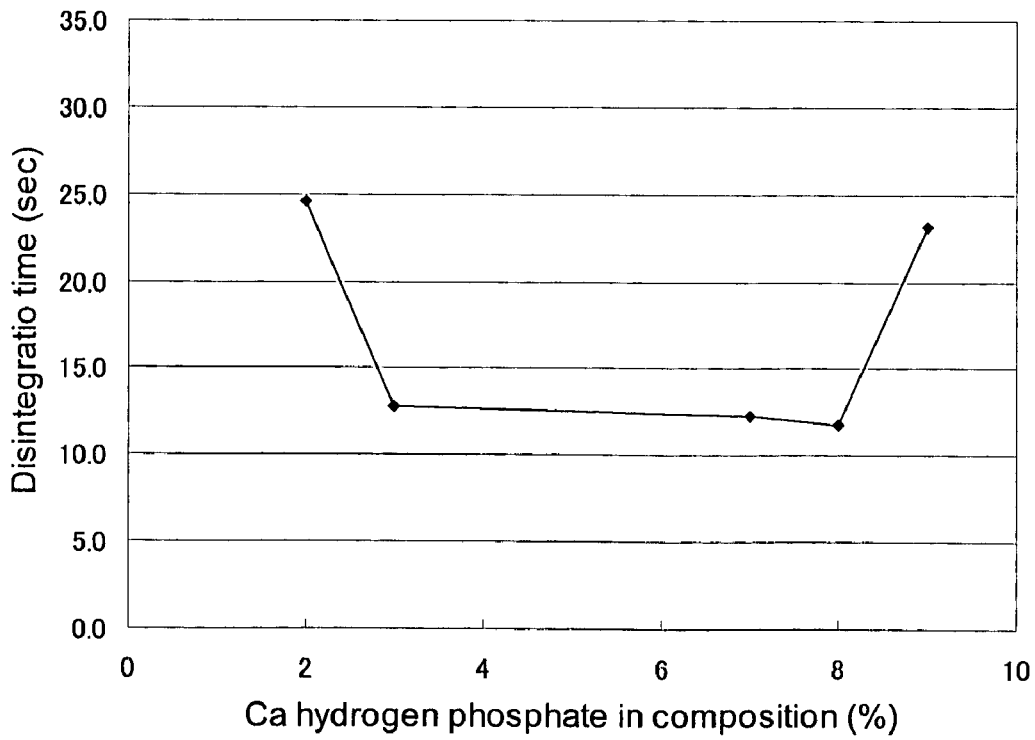
FIG. 6 is a graph where disintegration time in oral cavity is plotted relative to the ratio of calcium hydrogen phosphate in the composition of the present invention.

Compositions and tablets were prepared using the formulations shown in Table 6 by the same manner as in Example 1. The disintegration time in oral cavity of the resulting tablets was measured (n=6). The result is shown in Table 6. The graph where the disintegration time in oral cavity was plotted to the amount of calcium hydrogen phosphate in the composition is shown in FIG. 6.

From the result of Table 6, it is noted that, in a composition containing mannitol, xylitol, crystalline cellulose, crospovidone and calcium hydrogen phosphate, the disintegration time in oral cavity of the resulting tablet is good when the ratio of calcium hydrogen phosphate in the composition is 2 to 9 parts by weight and that it is particularly good when the ratio of calcium hydrogen phosphate in the composition is 3 to 8 parts by weight.

Example 7

Figure 7:
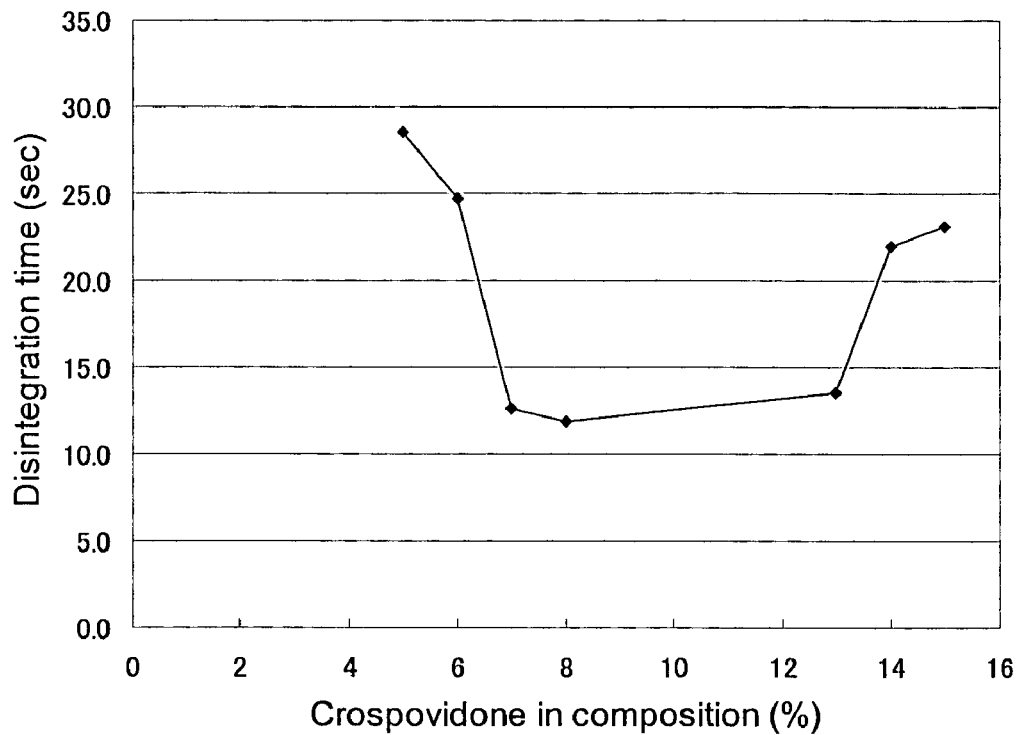
FIG. 7 is a graph where disintegration time in oral cavity is plotted relative to the ratio of crospovidone in the composition of the present invention.

Compositions and tablets were prepared using the formulations shown in Table 7 by the same manner as in Example 1. Disintegration time in oral cavity of the resulting tablets was measured (n=6). The result is shown in Table 7. The graph where the disintegration time in oral cavity was plotted to the amount of crospovidone in the composition is shown in FIG. 7.

TABLE 6

| | | Examples | | | | |
| --- | --- | --- | --- | --- | --- | --- |
| | | 6-1 | 6-2 | 6-3 | 6-4 | 6-5 |
| Formulation (g) | Mannitol | 668.5 | 659.5 | 622.0 | 613.0 | 604.0 |
| | Xylitol | 51.5 | 50.5 | 48.0 | 47.0 | 46.0 |
| | Crystalline cellulose | 180.0 | 180.0 | 180.0 | 180.0 | 180.0 |
| | Crospovidone | 80.0 | 80.0 | 80.0 | 80.0 | 80.0 |
| | Ca hydrogen phosphate | 20.0 | 30.0 | 70.0 | 80.0 | 90.0 |
| | Total | 1000.0 | 1000.0 | 1000.0 | 1000.0 | 1000.0 |
| | Disintegration time in oral cavity (sec) | 24.6 | 12.8 | 12.3 | 11.7 | 23.2 |

TABLE 7

|  |  | \multicolumn{7}{c}{Examples} |
| --- | --- | --- | --- | --- | --- | --- | --- | --- |
|  |  | 7-1 | 7-2 | 7-3 | 7-4 | 7-5 | 7-6 | 7-7 |
| Formulation (g) | Mannitol | 678.0 | 669.0 | 659.5 | 650.0 | 604.0 | 594.5 | 585.0 |
|  | Xylitol | 52.0 | 51.0 | 50.5 | 50.0 | 46.0 | 45.5 | 45.0 |
|  | Crystalline cellulose | 180.0 | 180.0 | 180.0 | 180.0 | 180.0 | 180.0 | 180.0 |
|  | Crospovidone | 50.0 | 60.0 | 70.0 | 80.0 | 130.0 | 140.0 | 150.0 |
|  | Ca hydrogen phosphate | 40.0 | 40.0 | 40.0 | 40.0 | 40.0 | 40.0 | 40.0 |
|  | Total | 1000.0 | 1000.0 | 1000.0 | 1000.0 | 1000.0 | 1000.0 | 1000.0 |
| Disintegration time in oral cavity (sec) |  | 28.5 | 24.7 | 12.6 | 11.9 | 13.5 | 22.0 | 23.1 |

From the result of Table 7, it is noted that, in a composition containing mannitol, xylitol, crystalline cellulose, crospovidone and calcium hydrogen phosphate, the disintegration time in oral cavity of the resulting tablet is good when the ratio of crospovidone in the composition is 6 to 15 parts by weight, that it is better when the ratio of crospovidone in the composition is 6 to 14 parts by weight and that it is particularly good when the ratio of crospovidone in the composition is 7 to 13 parts by weight.

Example 8

Figure 8:
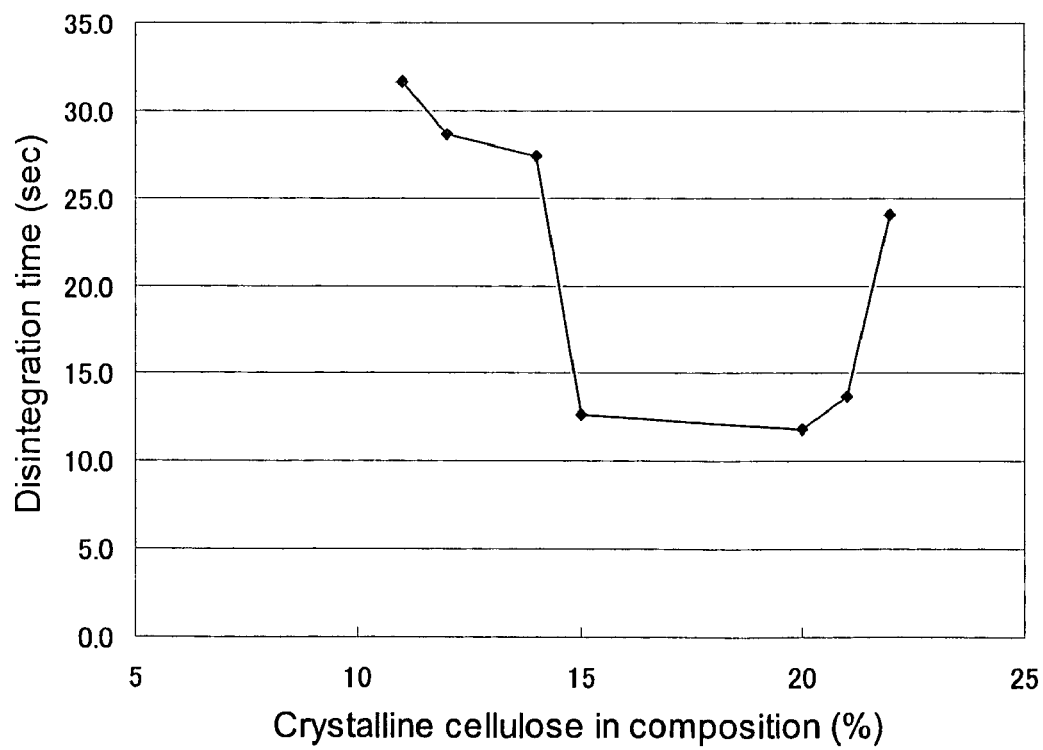
FIG. 8 is a graph where disintegration time in oral cavity is plotted relative to the ratio of crystalline cellulose in the composition of the present invention.

Compositions and tablets were prepared using the formulations shown in Table 8 by the same manner as in Example 1. Disintegration time in oral cavity of the resulting tablets was measured (n=6). The result is shown in Table 8. The graph where the disintegration time in oral cavity was plotted to the amount of crystalline cellulose in the composition is shown in FIG. 8.

TABLE 8

|  |  | \multicolumn{7}{c}{Examples} |
| --- | --- | --- | --- | --- | --- | --- | --- | --- |
|  |  | 8-1 | 8-2 | 8-3 | 8-4 | 8-5 | 8-6 | 8-7 |
| Formulation (g) | Mannitol | 715.0 | 705.5 | 687.0 | 678.0 | 631.5 | 622.0 | 613.0 |
|  | Xylitol | 55.0 | 54.5 | 53.0 | 52.0 | 48.5 | 48.0 | 47.0 |
|  | Crystalline cellulose | 110.0 | 120.0 | 140.0 | 150.0 | 200.0 | 210.0 | 220.0 |
|  | Crospovidone | 80.0 | 80.0 | 80.0 | 80.0 | 80.0 | 80.0 | 80.0 |
|  | Ca hydrogen phosphate | 40.0 | 40.0 | 40.0 | 40.0 | 40.0 | 40.0 | 40.0 |
|  | Total | 1000.0 | 1000.0 | 1000.0 | 1000.0 | 1000.0 | 1000.0 | 1000.0 |
| Disintegration time in oral cavity (sec) |  | 31.7 | 28.7 | 27.4 | 12.7 | 11.8 | 13.7 | 24.0 |

From the result of Table 8, it is noted that, in a composition containing mannitol, xylitol, crystalline cellulose, crospovidone and calcium hydrogen phosphate, the disintegration time in oral cavity of the resulting tablet is good when the ratio of crystalline cellulose in the composition is 14 to 22 parts by weight and that it is better when the ratio of crystalline cellulose in the composition is 15 to 21 parts by weight.

Example 9

Compositions and tablets were prepared by the same manner as in Example 1 according to the formulation shown in Table 9 using hydrotalcite and precipitated calcium carbonate as inorganic excipients. Disintegration time in oral cavity of the resulting tablets was measured (n=6). The result is shown in Table 9.

TABLE 9

|  |  | \multicolumn{2}{c}{Examples} |
| --- | --- | --- | --- |
|  |  | 9-1 | 9-2 |
| Formulation (g) | Mannitol | 650.0 | 650.0 |
|  | Xylitol | 50.0 | 50.0 |
|  | Crystalline cellulose | 150.0 | 150.0 |
|  | Crospovidone | 80.0 | 80.0 |
|  | Hydrotalcite | 70.0 |  |
|  | Calcium carbonate |  | 70.0 |
|  | Total | 1000.0 | 1000.0 |
| Disintegration time in oral cavity (sec) |  | 15.3 | 13.4 |

Example 10

Compositions prepared in Example 1 shown under 1-3, 1-4, 1-5 and 1-9 of Table 1 and a composition prepared by the same manner as in Example 1 using the formulation shown in Table 10 were used for the measurement of endothermic peak of the saccharides using a differential scanning calorimeter (TAS-200; manufacture by Rigaku Denki). The result is shown in Table 10.

TABLE 10

|  |  | Examples | | | | |
|---|---|---|---|---|---|---|
|  |  | 1-3 | 1-4 | 1-5 | 1-9 | 10 |
| Formulation (g) | Mannitol | 672.0 | 650.0 | 630.0 | 602.0 | 400.0 |
|  | Xylitol | 28.0 | 50.0 | 70.0 | 98.0 | 300.0 |
|  | Xylitol in saccharides | 4% | 7% | 10% | 14% | 43% |
|  | Crystalline cellulose | 150.0 | 150.0 | 150.0 | 150.0 | 150.0 |
|  | Crospovidone | 80.0 | 80.0 | 80.0 | 80.0 | 80.0 |
|  | Mg aluminometasilicate | 70.0 | 70.0 | 70.0 | 70.0 | 70.0 |
|  | Total | 1000.0 | 1000.0 | 1000.0 | 1000.0 | 1000.0 |
| Endothermic peak of saccharides(° C.) |  | 166.4 | 164.2 | 161.7 | 158.4 | 142.1 |
| Disintegration time in oral cavity (sec) |  | 14.4 | 13.2 | 13.9 | 25.7 | 98.0 |

When mannitol (Mannit P; manufactured by Towa Kasei Kogyo) used as the material was measured by a differential scanning calorimeter, an endothermic peak of mannitol was 168.8° C.

From the result of Table 10, it is noted that, when melting point (endothermic peak) of saccharides is shifted to an extent of 0.5 to 19° C. or, preferably 1 to 9° C., to a low-temperature side as compared with melting point of mannitol, disintegration time in oral cavity is particularly good.

Example 11

The composition shown as 1-4 in Table 1 prepared in Example 1 and the composition shown as 5-4 in Table 5 prepared in Example 5 were subjected to measurement of capping rate upon compression molding using a tabletting tester (SK-2; manufactured by Sankyo Pio-Tech Co., Ltd.). The result is shown in Table 11.

TABLE 11

|  |  | Examples | |
|---|---|---|---|
|  |  | 1-4 | 5-4 |
| Formulation (g) | Mannitol | 650.0 | 630.0 |
|  | Xylitol | 50.0 | 70.0 |
|  | Crystalline cellulose | 150.0 | 180.0 |
|  | Crospovidone | 80.0 | 80.0 |
|  | Mg aluminometasilicate | 70.0 |  |
|  | Ca hydrogen phosphate |  | 40.0 |
|  | Total | 1000.0 | 1000.0 |
|  | Capping rate | 0.939 | 0.950 |

Example 12

Xylitol (50 g) was completely dissolved in 1500 mL of water, 650 g of mannitol was then added and the mixture was stirred at room temperature at 200 to 300 rpm for 60 minutes using a wet dispersing device (Mycolloider type M; manufactured by Tokushu Kika Kogyo Co., Ltd.) to give a dispersion in which mannitol was homogeneously dispersed. To the dispersion were added 80 g of crospovidone, 150 g of crystalline cellulose and 70 g of magnesium aluminometasilicate and, after the mixture was homogeneously dispersed, it was spray-dried using a spray-dryer (type L-8; manufactured by Okawahara Kakohki Co., Ltd.) with an inlet temperature of 150° C. and an outlet temperature of 100° C. to give white granules 1.

The resulting granules 1, L-ascorbic acid as a pharmacologically active ingredient and magnesium stearate as a component which does not deteriorate the disintegrating property were mixed in an amount shown in Table 12 and tabletted using a rotary tablet machine (with a punch of 8 mm diameter where corners were flat) to prepare tablets each weighing 200 mg and having a tablet hardness of 3.5 kg. Disintegration time in oral cavity of the resulting tablet and the existence of the tabletting troubles are shown in Table 12.

TABLE 12

| Formulation (g) | Granule 1 | 447.0 | 397.0 | 297.0 |
|---|---|---|---|---|
|  | L-ascorbic acid | 50.0 | 100.0 | 200.0 |
|  | Magnesium stearate | 3.0 | 3.0 | 3.0 |
| Tabletting pressure (kgf) |  | 290 | 350 | 600 |
| Hardness of tablets (kg) |  | 3.5 | 3.5 | 3.4 |
| Tabletting troubles |  | None | None | None |
| Disintegration time in oral cavity (sec) |  | 12 | 14 | 19 |

Example 13

Tablets were prepared by the same manner as in Example 12 except that acetaminophen was used instead of L-ascorbic acid. The disintegration time in oral cavity of the resulting tablet and the existence of the tabletting troubles are shown in Table 13.

TABLE 13

| Formulation (g) | Granule 1 | 447.0 | 397.0 | 297.0 |
|---|---|---|---|---|
|  | Acetaminophen | 50.0 | 100.0 | 200.0 |
|  | Magnesium stearate | 3.0 | 3.0 | 3.0 |
| Tabletting pressure (kgf) |  | 300 | 340 | 600 |
| Hardness of tablets (kg) |  | 3.5 | 3.6 | 3.4 |
| Tabletting troubles |  | None | None | None |
| Disintegration time in oral cavity (sec) |  | 13 | 14 | 18 |

Example 14

Figure 9:
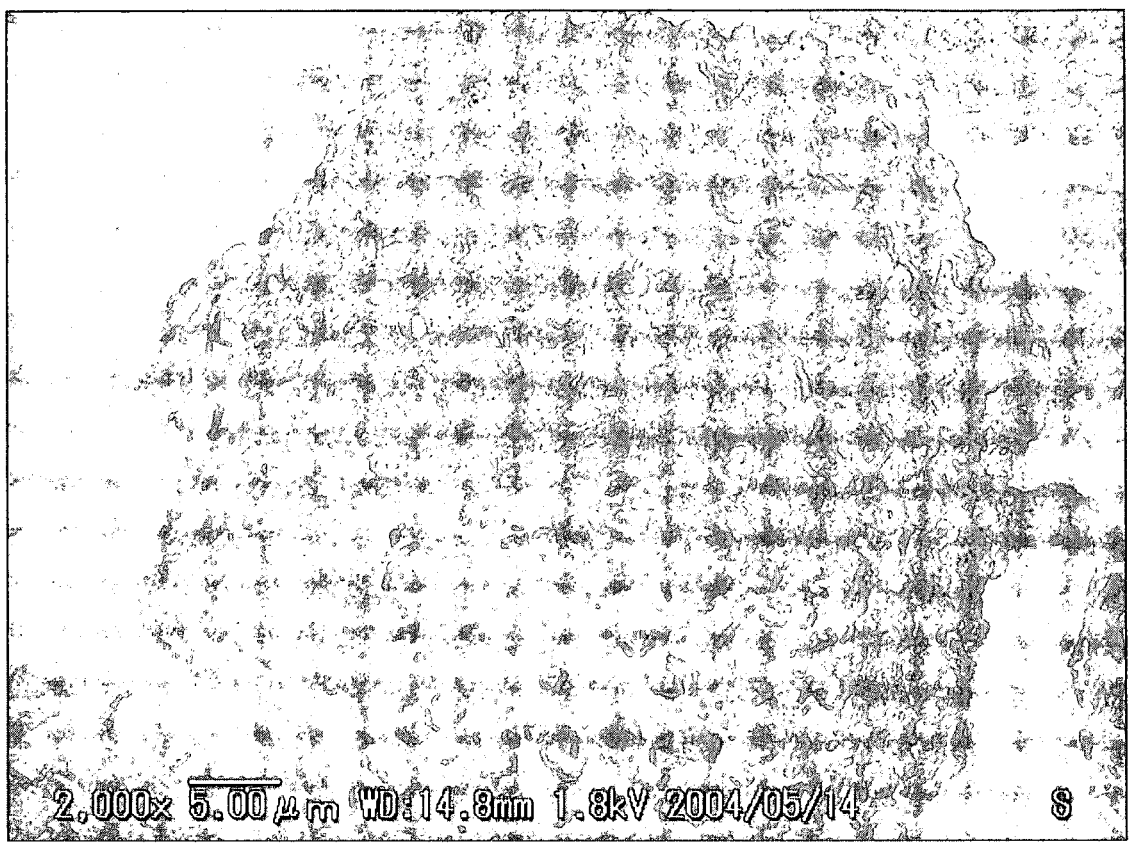
FIG. 9 is a picture of the granules 2, which was prepared in Example 14 of the present specification, observed under a scanning electron microscope.

Xylitol (50 g) was completely dissolved in 1500 mL of water, 650 g of mannitol was then added and the mixture was stirred at room temperature at 200 to 300 rpm for 60 minutes using a wet dispersing device (Mycolloider type M; manufactured by Tokushu Kika Kogyo Co., Ltd.) to give a dispersion in which mannitol was homogeneously dispersed. To the dispersion were added 80 g of crospovidone, 180 g of crystalline cellulose and 40 g of calcium hydrogen phosphate and, after the mixture was homogeneously dispersed, it was spray-dried using a spray-dryer (type L-8; manufactured by Okawahara Kakohki, Co., Ltd.) where an inlet temperature was 150° C. and an outlet temperature was 100° C. to give white granules 2. FIG. 9 shows a picture of the granules 2 under a scanning electron microscope (manufactured by Keyence Corp.). It is noted from FIG. 9 that particles of about 2 μm and particles of about 5 μm are present, and they are homogeneously dispersed without aggregation on the surface of the composition of the invention.

The resulting granules 2, L-ascorbic acid and magnesium stearate were mixed in an amount shown in Table 14 and tabletted using a rotary tablet machine (with a punch of 8 mm diameter where corners were flat) to prepare tablets each weighing 200 mg and having a tablet hardness of 3.5 kg. Disintegration time in oral cavity of the resulting tablet and the existence of the tabletting troubles are shown in Table 14.

TABLE 14

| Formulation (g) | Granule 2 | 447.0 | 397.0 | 347.0 |
|---|---|---|---|---|
|  | L-ascorbic acid | 50.0 | 100.0 | 150.0 |
|  | Magnesium stearate | 3.0 | 3.0 | 3.0 |
| Tabletting pressure (kgf) | | 250 | 280 | 400 |
| Hardness of tablets (kg) | | 3.4 | 3.4 | 3.4 |
| Tabletting troubles | | None | None | None |
| Disintegration time in oral cavity (sec) | | 9 | 10 | 16 |

Tablets were prepared by the same manner as in Example 12 except that acetaminophen was used instead of L-ascorbic acid. The disintegration time in oral cavity of the resulting tablet and the existence of the tabletting troubles are shown in Table 15.

TABLE 15

| Formulation (g) | Granule 2 | 447.0 | 397.0 | 347.0 |
|---|---|---|---|---|
|  | Acetaminophen | 50.0 | 100.0 | 150.0 |
|  | Magnesium stearate | 3.0 | 3.0 | 3.0 |
| Tabletting pressure (kgf) | | 270 | 320 | 450 |
| Hardness of tablets (kg) | | 3.4 | 3.5 | 3.4 |
| Tabletting troubles | | None | None | None |
| Disintegration time in oral cavity (sec) | | 10 | 10 | 14 |

Reference Example 1

Tablets were prepared according to the method described in Japanese Unexamined Patent Publication No. Hei 10(1998)-120554. Thus, hydrotalcite, sorbitol, xylitol, cornstarch, aspartame and methyl paraben according to an amount shown in Table 16 were made into a slurry and spray-dried, 0.5 part by weight of magnesium stearate was added thereto and the mixture was tabletted using a rotary tablet machine to give tablets each weighing 200 mg and having a diameter of 8 mm. Granules prepared by the spray-drying were very bulky and weights of the resulting tablets were significantly varied and, therefore, velocity of the rotary tablet machine was lowered and tabletting pressure was set to 100 kg/cm² and 200 kg/cm² to obtain the tablets. Disintegration test in oral cavity was conducted for the resulting tablets. The result is shown in Table 17.

TABLE 16

| Hydrotalcite | 85.0 |
|---|---|
| Sorbitol | 5.0 |

TABLE 16-continued

| Xylitol | 5.0 |
|---|---|
| Cornstarch | 4.8 |
| Aspartame | 0.1 |
| Methylparaben | 0.1 |
| Total | 100.0 |

TABLE 17

| | Hardness of Tablets | |
|---|---|---|
| | 3.0 kg | 7.5 kg |
| Tabletting pressure (kgf) | 100 | 200 |
| Disintegration time in oral cavity (sec) | >180 | >180 |

Industrial Applicability

Although the tablets which are prepared by using the composition for the rapid disintegrating tablets in oral cavity according to the present invention have higher hardness than the conventional rapid disintegrating tablets, they still have an advantage that disintegration time in oral cavity can be significantly shortened. Accordingly, the rapid disintegrating tablets in oral cavity according to the present invention which is obtained by admixing a pharmacologically active ingredient with the composition are suitable for pharmaceuticals and foods which are demanded to have a rapid disintegrating property in oral cavity. The composition and the tablets of the present invention are able to be prepared by using conventional tablet-manufacturing lines and are able to be manufactured by a method having an excellent productivity where no special step is necessary.

The composition for the rapid disintegrating tablets in oral cavity according to the present invention makes it possible to obtain tablets having particularly excellent disintegration in oral cavity and can be appropriately used for tablets which are demanded to show a rapid disintegration in oral cavity.

The invention claimed is:

1. A composition for rapid disintegrating tablets in oral cavity comprising
    (a) a combination of mannitol and xylitol in an amount of 40 to 90 parts by weight of the composition;
    (b) an inorganic excipient in an amount of 1 to 30 parts by weight of the composition; and
    (c) a disintegrating agent in an amount of 5 to 40 parts by weight of the composition,
    wherein the total amount of (a), (b) and (c) is 100 parts by weight of the composition
    wherein the ratio by weight of mannitol to xylitol is (98 to 67):(2 to 33)
    wherein mannitol and xylitol form complex particles and the inorganic excipient and the disintegrating agent are homogenously dispersed in the complex particles, and
    wherein the composition is obtained by spray-drying an aqueous solution or an aqueous dispersion comprising components (a) to (c).

2. The composition according to claim 1, which contains 50 to 80 parts by weight of the composition of the mannitol and xylitol.

3. The composition according to claim 1, which contains 62 to 78 parts by weight of the composition of the mannitol and xylitol.

4. The composition according to claim 1, wherein the ratio by weight of mannitol to xylitol is (97 to 87):(3 to 13).

5. The composition according to claim 1, wherein the ratio by weight of mannitol to xylitol is (96 to 89):(4 to 11).

6. The composition according to claim 1, which contains 2 to 15 parts by weight of the inorganic excipient.

7. The composition according to claim 1, which contains 2 to 9 parts by weight of the inorganic excipient.

8. The composition according to claim 1, which contains 3 to 8 parts by weight of the inorganic excipient.

9. The composition according to claim 1, wherein the inorganic excipient is a pharmaceutically acceptable inorganic compound containing any of aluminum, magnesium and calcium.

10. The composition according to claim 9, wherein the inorganic excipient is selected from magnesium aluminometasilicate, magnesium aluminosilicate, calcium hydrogen phosphate, talc, dry aluminum hydroxide gel, hydrotalcite, calcium carbonate and calcium silicate.

11. The composition according to claim 9, wherein the inorganic excipient is selected from magnesium aluminometasilicate, calcium carbonate, hydrotalcite and calcium hydrogen phosphate.

12. The composition according to claim 1, which contains 10 to 36 parts by weight of the disintegrating agent.

13. The composition according to claim 1, which contains 16 to 35 parts by weight of the disintegrating agent.

14. The composition according to claim 1, which contains 18 to 34 parts by weight of the disintegrating agent.

15. The composition according to claim 1, wherein the disintegrating agent is selected from crospovidone, low-substituted hydroxypropyl cellulose, croscarmellose sodium and crystalline cellulose.

16. The composition according to claim 1, wherein the disintegrating agent is crospovidone, crystalline cellulose, or both.

17. The composition according to claim 16, which contains 5 to 15 parts by weight of crospovidone and 10 to 22 parts by weight of the composition of crystalline cellulose as the disintegrating agent.

18. The composition according to claim 16, which contains 6 to 13 parts by weight of crospovidone and 12 to 21 parts by weight of the composition of crystalline cellulose as the disintegrating agent.

19. The composition according to claim 1, wherein the mannitol and xylitol form a solid dispersion and a fine disintegrating agent and a fine inorganic excipient are dispersed in the solid dispersion.

20. The composition according to claim 19, wherein the disintegrating agent and the inorganic excipient have an average particle diameter of 1 to 40 µm, respectively.

21. The composition according to claim 1, wherein an endothermic peak of the mannitol and xylitol measured by a differential scanning calorimeter is shifted to a low temperature side by 0.5 to 19° C. compared to an endothermic peak measured from mannitol only.

22. The composition according to claim 1, wherein an endothermic peak of the mannitol and xylitol measured by a differential scanning colorimeter is shifted to a low temperature side by 1 to 9° C. compared to an endothermic peak measured from mannitol only.

23. The composition according to claim 1, wherein an endothermic peak of the mannitol and xylitol measured by a differential scanning colorimeter is shifted to a low temperature side by 1 to 8° C. compared to an endothermic peak measured from mannitol only.

24. The composition according to, claim 1 wherein a capping rate measured upon compression molding is 0.85 to 1.00.

25. The composition according to claim 1, wherein a capping rate measured upon compression molding is 0.90 to 1.00.

26. The composition according to claim 1, wherein the composition has an average particle diameter is 30 to 200 .µm, a repose angle is 27 to 40°, and a static specific volume is 1.5 to 2.5 mL/g.

27. The composition according to claim 1, which is obtained by spray-drying the dispersion obtained by dissolving or dispersing, in advance, mannitol and xylitol in an aqueous medium and then homogeneously dispersing the disintegrating agent and the inorganic excipient.

28. The composition according to claim 1, which further comprises 0.01 to 100 parts by weight of a pharmacologically active ingredient and/or 0.01 to 1000 parts by weight of a component which does not deteriorate a disintegrating property based on 100 parts by weight relative to the a total amount of mannitol, xylitol, the inorganic excipient and the disintegrating agent.

29. A rapid disintegrating tablet in oral cavity as prepared by using the composition according to claim 1, which further comprises 0.01 to 100 parts by weight of the composition of a pharmacologically active ingredient and/or 0.01 to 1000 parts by weight of the composition of a component which does not deteriorate a disintegrating property based on 100 parts by weight of the composition of the composition.

* * * * *